United States Patent [19]

Nishi et al.

[11] Patent Number: 5,620,685
[45] Date of Patent: Apr. 15, 1997

[54] PROTECTING AGENTS FROM RADIATION HAZARDS

[75] Inventors: Nobusuke Nishi, Maebashi; Haruhiko Tsumura, Tano-gun; Hideo Inoue, Takasaki, all of Japan

[73] Assignee: Kirin Brewery Company, Limited, Tokyo, Japan

[21] Appl. No.: 357,125

[22] Filed: Dec. 16, 1994

[30] Foreign Application Priority Data

Dec. 16, 1993 [JP] Japan ................................. 5-316914

[51] Int. Cl.$^6$ ..................... A61K 38/18; A61K 38/19; A61K 38/20

[52] U.S. Cl. ................. 424/85.1; 424/85.2; 424/85.4; 514/8

[58] Field of Search ........................ 514/8; 424/85.1, 424/85.2, 85.4

[56] References Cited

FOREIGN PATENT DOCUMENTS

| 0350641A2 | 1/1990 | European Pat. Off. . |
| 0410750A2 | 1/1991 | European Pat. Off. . |
| WO91/05795 | 5/1991 | WIPO . |

OTHER PUBLICATIONS

Jones et al, Nature, 347, 13 Sep. 1990, pp. 188–189.
Neta et al. *Journal of Immun.*, "Interdependence of the Radioprotective effects of Human Recombinant Interleukin" vol. 140, pp. 108–111, Jan. 1988.

*Primary Examiner*—Howard E. Schain
*Attorney, Agent, or Firm*—Foley & Lardner

[57] ABSTRACT

The present invention relates to pharmaceutical composition comprising SCF protein, IL-3 protein, GM-CSF protein and IL-6 protein. More specifically, the present invention relates to a protecting agent from radiation hazards, comprising SCF protein, IL-3 protein, GM-CSF protein and IL-6 protein.

The present invention also relates to a method for the treatment of patients with radiation hazards, which comprises administering the pharmaceutical composition according in a therapeutically effective amount to the patients.

The present invention has an excellent effect of enabling 100% survival of animals exposed to a lethal dose of radiations, which could not be attained by prior art pharmaceuticals.

10 Claims, 1 Drawing Sheet

PROTECTING AGENTS FROM RADIATION HAZARDS

BACKGROUND OF THE INVENTION

1. Field of the Invention

This invention relates to a pharmaceutical composition for the treatment of radiation hazards, in which SCF (stem cell factor) protein, IL-3 (interleukin-3) protein, GM-CSF (granulocyte macrophage colony stimulating factor) protein and IL-6 (interleukin-6) protein are comprised in combination as the active components.

This invention also relates to a method for the treatment of patients with radiation hazards using such a pharmaceutical composition.

2. Prior Art

Radiations, e.g. α-, β- and γ-rays released from radioactive materials, or X-ray, proton beam, neutron beam and electron beam which are artificially produced, cause the abnormality of the cell division system in living cells thus resulting in lack of the ability of the cell growth. Cells are destroyed normally when exposed to an excess dose of the radiations. It is assumed that disorders in the central nervous system occur in a dose of 50 Gy or more, intestinal disorders in a dose of 10 Gy or more, and hematopoietic disorders in a dose of from 6 Gy to 10 Gy, thereby leading to the death of living bodies ("Gy" is a unit of absorbed radiation dose). Thus, the hematopoietic tissues or cells, particularly bone marrow cells, have the highest radiation sensitivity in the living body. The term "bone marrow cells" as used herein is referred to cells at various differentiation stages which exist in the bone marrow, such as erythrocytes, neutrophils, eosinophils, basophils, monocytes and thrombocytes.

When exposed to a radiation, the numbers of peripheral blood cells, especially leukocytes and thrombocytes, decrease sharply affecting the living body's survival. Hence, the bone marrow transplantation is an effective curative treatment when the living body is exposed to a radiation of 6 Gy or more. In the bone marrow transplantation, the human leucocyte antigen (HLA) in the bone marrow of a donor and that of a recipient should coincide with each other, since the incompatibility of HLA causes a graft-versus-host disease (GVED). In the present situation, however, it is extremely difficult to obtain bone marrow cells having compatibility of HLA.

With the popularization of nuclear power generation and the development of atomic industries such as nuclear fuel treatment, the possibility of causing exposure accidents has now been increasing among people engaged in radiation-operating works. Also, by the accident at the nuclear plant in Chernovuiri, inhabitants, as well as for example domestic animals, in the neighboring region have undergone serious influences. When exposed to such strong radiations, however, there are no available drugs which can protect from the radiation hazards effectively.

Current therapies for the treatment of malignancies are associated with significant damages to the hematopoietic system since radiation therapy do not discriminate between malignant cells and normal cells. This results in cessation of blood cell production leading to pancytopenia. Lymphocytes are depressed most rapidly followed by leukocytes, thrombocytes and erythrocytes. Then clinical problems such as decreased resistance to infection, anemia, and bleeding occur. At the same time, medical workers such as X-ray technicians, physicians have a chance to be irradiated while they work, these problems are not only for malignant patients but also for medical workers.

In recent years, several methods have been proposed which use certain substances that have a surviving effect from lethal cause, such as IL-1 (interleukin-1) (Neta, R. et al., *J. Immunol.*, vol.136, p.2483, 1986; and Aihara, K. et al., U.S. Pat. No. 5,120,534), G-CSF (granulocyte colony stimulating factor) (Tanigawa, S. et al., *Blood*, vol.76, p.445, 1990), SCF (stem cell factor, Zsebo, K. M. et al., WO91/05795), ammonium trichloro(dioxoethylene-O,O')tellurate known as an immunomodulator (Kalechman, Y. et al., *J. Immunol.*, vol.145, p.1512, 1990; JP-A-2-200630), nonapeptide known as a serum thymic factor (JP-A-2-36126), a cimetidine-copper complex (JP-A-1-153640), and 2-phenyl-1,2-benzoisoselenazol-3(2H)-one (JP-A-1-135718). However, there are in fact still great demands on radiation protecting agents which have superior effects to the prior art agents.

In this connection, several treatment methods have also been proposed in which combinations of growth factors are used to attain their synergistic effect: for example, combination of GM-CSF, G-CSF, IL-6, IL-5 (interleukin-5) and IL-3 for production of megakaryocytes (WO 91/07988); combination of MMF (megakaryocyte maturating factor), SCF, G-CSF, IL-3, Meg-CSF (megakaryocyte colony stimulating factor) and Epo (erythropoietin) (WO 92/06712) or combination of IL-7 (interleukin-7), IL-1α (interleukin-1α), IL-1β, IL-3, IL-4 (interleukin-4), IL-6, Epo, GM-CSF and G-CSF (WO 90/09194) for treatment of thrombocytopenia; and combination of IL-4, GM-CSF, G-CSF, IL-1, IL-2 (interleukin-2), IL-3, IL-5, IL-6 and IFN (interferon)-α (EP/410750) or combination of BCDF (B cell differentiation factor), IL-1, IL-3, IL-4, G-CSF, GM-CSF and M-CSF (macrophage colony stimulating factor) (EP 350641) or combination of IL-1α, TNF (tumor necrosis factor) α, G-CSF and GM-CSF (Neta, R. et al., *J. Immunol.*, vol.140, p.108, 1988) for radiation protection.

We have studied on the most efficient radiation protection among various combinations of growth factors and found that the specific combination of SCF, IL-3, GM-CSF and IL-6 shows a markedly high radiation protection after exposure to radiations.

SUMMARY OF THE INVENTION

This invention therefore provides a pharmaceutical composition comprising SCF protein, IL-3 protein, GM-CSF protein and IL-6 protein. More specifically, this invention provides a protecting agent from radiation hazards, comprising SCF protein, IL-3 protein, GM-CSF protein and IL-6 protein.

This invention also provides a method for the treatment of patients with radiation hazards, which comprises administering the pharmaceutical composition in a therapeutically effective amount to the patients.

DETAILED DESCRIPTION OF THE INVENTION

Figure 1:
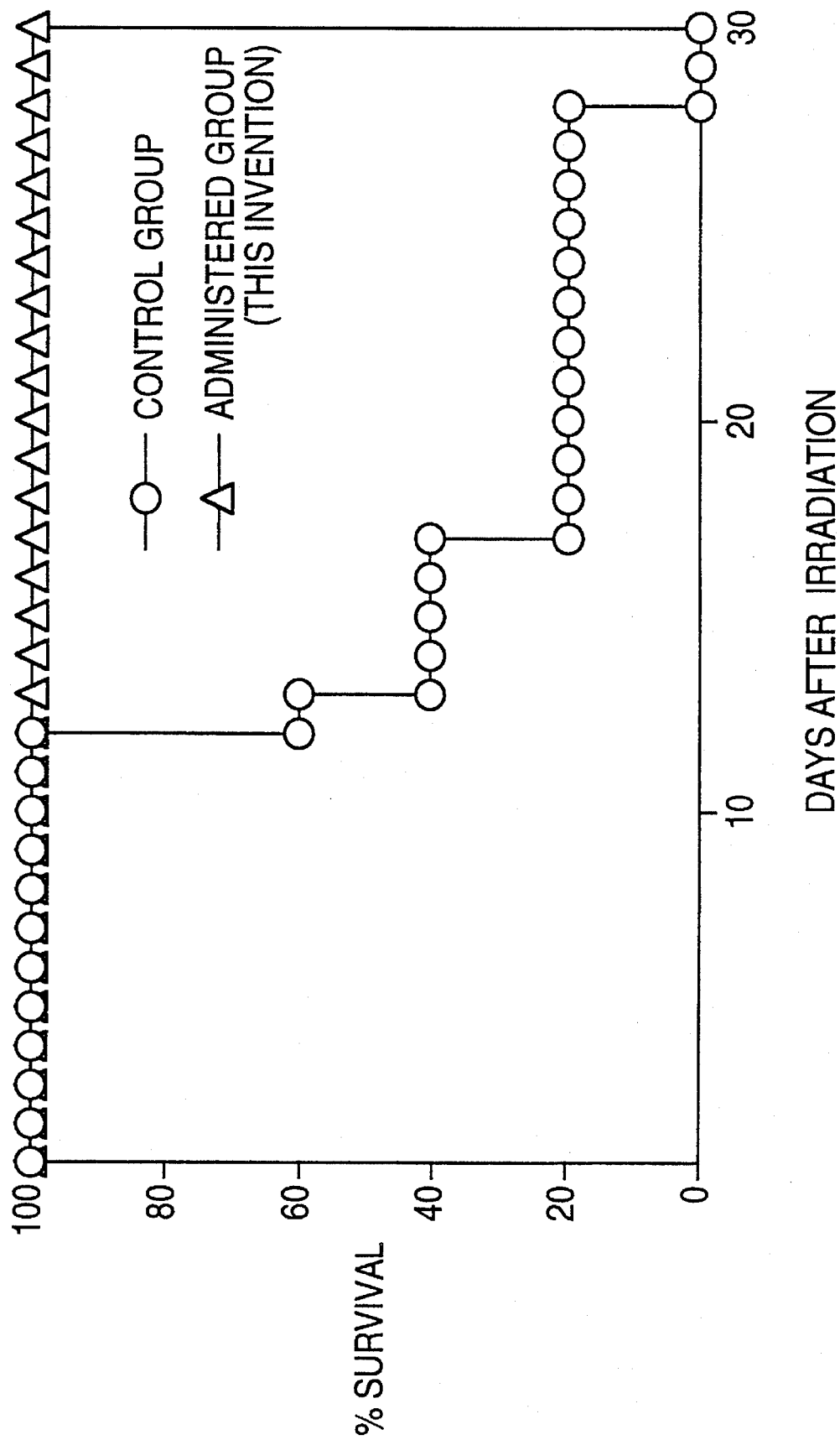
FIG. 1 is a graph showing the relationship between days after X-ray irradiation and % survival of mice.

SCF protein is a stroma cell-derived glycoprotein isolated as a ligand for the product from c-kit gene, and it is also called MGF (Williams, D. E. et al., *Cell*, vol.63, p.167, 1990), KL (Huang, E. et al., *Cell*, vol.63, p.225, 1990) or Steel Factor (Witte, O. N. et al., *Cell*, vol.63, p.5, 1990). SCF protein has been found in rodents and human in mammals, which can stimulate the growth of the stem cell which can differentiate into all kinds of blood cells or mast cells. According to the present invention, any one of vertebrate-derived SCFs, preferably mammalian-derived SCF proteins, such as murine SCF protein, human SCF protein and the like can be used. Apart from the difference in their origins, the SCFs have the same function (Migliaccio, G. et al., *Blood*, vol.79, p.2620, 1992; Tauji, K. et al., *Blood*, vol.78, p.1223, 1991). However, human SCF protein may be used more preferably when the antigenicity at the time of administration into human body is taken into consideration. The term "murine SCF protein" as used herein means a glycoprotein which is composed of 248 amino acids and has a molecular weight of 70 to 90 Kd (Williams, D. E. et al., Cell, vol. 63, p. 167, 1990, Zsebo, K. M. et al., Cell, vol. 63, p. 195, 1990; Huang, E. et al., Cell, vol. 63, p. 225, 1990), and the term "human SCF protein" means a glycoprotein which is composed of 248 amino acids (Zsebo, K. M. et al., JP-A-4-502628, Martin, F. H. et al., Cell, vol. 63, p. 203, 1990; WO 91/05795). The SCF proteins used in the present invention include not only those which have the known amino acid sequences as such but also those in which the sequences are modified by substitution, deletion or addition, provided that they have the SCF activity. Though not particularly limited to, the murine SCF protein is used in the Examples set forth below with taking the species specificity into consideration because of the necessity to carry out in vivo tests in mice.

IL-3 protein is a glycoprotein which is isolated as a member of T cell-derived cytokines found in rodents and human in mammals. The IL-3 protein is known to have the activity, in both mouse and human, to enhance the differentiation and proliferation of undifferentiated hematopoietic precursor cells or the colony formation of mast cells, macrophages, granulocytes, megakaryocytes or erythroblasts. According to the present invention, any one of the vertebrate-derived IL-3 proteins, preferably mammalian-derived IL-3 proteins, such as murine IL-3 protein, human IL-3 protein and the like can be used. Apart from the difference in their origins, the IL-3 protein members have the same function (Hapel, A. J. et al., *Blood*, vol. 65, p. 1453, 1985; Suda, T. et al., *J. Cell Physiol.*, vol. 124, p. 182, 1985; Leary, A. G. et al., *Blood*, vol. 75, p. 1960, 1990). When the antigenicity at the time of administration into human bodies is taken into consideration, human IL-3 protein may be used more preferably. The term "murine IL-3 protein" as used herein means a glycoprotein which is composed of 140 amino acids and has a molecular weight of approximately 28,000 (Fung, M. C. et al., *Nature*, vol. 307, p. 233, 1984), and the term "human IL-3 protein" means a glycoprotein which is composed of 133 amino acids (Yang, Y. C. et al., *Cell*, vol. 47, p. 3, 1986). The IL-3 proteins used in the present invention include not only those which have the known amino acid sequences as such but also those in which the sequences are modified by substitution, deletion or addition, provided that they have the IL-3 activity. Though not particularly limited to, the murine IL-3 protein is used in the Examples set forth below with taking the species specificity into consideration because of the necessity to carry out in vivo tests in mice.

GM-CSF protein is a glycoprotein isolated as a member of colony stimulating factors (CSFs), which can be found in rodents and human in mammals, and it has the activity, in both mouse and human, to enhance the colony formation of macrophages, granulocytes, eosinophils or megakaryocytes. According to the present invention, any one of the vertebrate-derived GM-CSF proteins, preferably mammalian-derived GM-CSF proteins, such as murine GM-CSF protein, human GM-CSF protein and the like can be used. Apart from the difference in their origins, the GM-CSF proteins have the same function (Metcalf, D. et al., *J. Cell Physiol.* vol. 128, p. 421, 1986; Robinson, B. E. et al., *J. Clin. Invest.*, vol. 79, p. 1648, 1987; Metcalf, D. et al., *Blood*, vol. 67, p. 37, 1986; Mazur, E. et al., *Exp. Hematol.*, vol. 15, p. 1128, 1987; Migliaccio, A. R. et al., *Blood*, vol. 70, p. 1867, 1987). When the antigenicity at the time of administration into human bodies is taken into consideration, the human GM-CSF protein may be used more preferably. The term "murine GM-CSF protein" as used herein means a glycoprotein which is composed of 124 amino acids and has a molecular weight of approximately 23,000 (Gough, N. M. et al., EMBO J., vol. 4, p. 645, 1985), and the term "human GM-CSF protein" means a glycoprotein which is composed of 127 amino acids and has a molecular weight of approximately 22,000 (Wong, G. G. et al., *Science*, vol. 228, p. 810, 1985). The GM-CSF proteins used in the present invention include not only those which have the known amino acid sequences as such but also those in which the sequences are modified by substitution, deletion or addition, provided that they have the GM-CSF activity. Though not particularly limited to, the murine GM-CSF protein is used in the Examples set forth below with taking the species specificity into consideration because of the necessity to carry out in vivo tests in mice.

IL-6 protein is a member of cytokines which can be found in rodents and human in mammals and exerts actions upon hematopcietic stem cells and megakaryocytes in addition to its function to induce differentiation of B-lymphocyte into antibody producing cells. According to the present invention, any one of the vertebrate-derived IL-6 proteins, preferably mammalian-derived IL-6 proteins, such as murine IL-6 protein, human IL-6 protein and the like can be used. Apart from the difference in their origins, the IL-6 proteins have the same function (Hirano, T. et al., *Proc. Natl. Acad. Sci. USA*, vol. 82, p. 5490, 1985; Ikebuchi, K. et al., *Proc. Natl. Acad. Sci. USA*, vol. 84, p. 9035, 1987; Ishibashi, T. et al., *Proc. Natl. Acad. Sci. USA*, vol. 86, p. 5953, 1988). When the antigenicity at the time of administration into human bodies is taken into consideration, human IL-6 protein may be used more preferably. The term "human IL-6 protein" as used herein means a glycoprotein which is composed of 184 amino acids and has a molecular weight of approximately 21,000 (Hirano, T. et al., *Nature*, vol. 324, p. 73, 1986), and the term "murine IL-6 protein" means a glycoprotein which is composed of 187 amino acids. The IL-6 protein is used in the present invention include not only those which have the known amino acid sequences as such but also those in which the sequences are modified by substitution, deletion or addition, provided that they have the IL-6 activity.

When the present invention is applied to medicaments, the pharmaceutical composition which comprises SCF protein, IL-3 protein, GM-CSF protein and IL-6 protein as active components in therapeutically effective amounts is prepared in a suitable dosage form and administered by oral or parenteral administration. The dosage may vary generally depending for example on the seriousness of symptoms of each disease; age, sex, body weight or sensitivity of each patient; method, time or interval of the administration; properties, formulation or type of each pharmaceutical preparation; or type of each active component. In the pharmaceutical preparation of the present invention, it may be administered generally in a dose of approximately 2 to 4 μg per kg adult's body weight per day, with dividing the daily dose into 1 to 3 portions.

The pharmaceutical composition of the present invention can be made into various dosage forms such as injections, suppositories, sublingual tablets, tablets, capsules or the like, in accordance with corresponding techniques conventionally used in the field of pharmaceuticals.

When injections are prepared, to the base agent may be added a pH adjusting agent, a buffering agent, a suspending agent, a solubilizing auxiliary agent, a stabilizing agent, a tonicity agent, a preservative or the like, and then formulated in the form of an intravenous, subcutaneous or intramuscular injection by conventional methods. If necessary, the pharmaceutical composition of the present invention may be prepared in the form of a freeze-dried preparation in usual ways.

Examples of the suspending agent include methylcellulose, Polysorbate 80, hydroxyethylcellulose, acacia, powdered tragacanth gum sodium, carboxymethylcellulose, polyoxyethylene sorbitan monolaurate and the like.

Examples of the solubilizing auxiliary agent include polyoxyethylene hydrogenated castor oil, Polysorbate 80, nicotinamide, polyoxyethylene sorbitan monolaurate, Macrogol, castor oil fatty acid ethyl ester and the like.

Examples of the stabilizing agent include sodium sulfite, sodium matasulfite, ethers and the like, and examples of the preservative include methyl paraoxybenzoate, ethyl paraoxybenzoate, sorbic acid, phenol, cresol, chlorocresol and the like.

There is a report that SCF protein has a radiation protecting effect (WO 91/05795). According to this report, however, average surviving day of radiation-exposed animals were prolonged for merely about 2 days in comparison with the control group, and all animals in the SCF protein-administered group died within 2 weeks after the exposure to lethal dose of radiation. On the contrary, as will be shown in the following test examples, the pharmaceutical composition of the present invention has an excellent effect of enabling 100% survival of animals exposed to a lethal dose of radiation, which could not be attained by the prior art agent.

The present invention will be illustrated in more detail by the following Examples to which it is not limited.

EXAMPLES

Example 1

Preparation of murine SCF protein

This Example relates to the expression in *Escherichia coli* of an SCF gene which encodes [Met$^{-1}$] murine SCF$^{2-164}$ protein (hereinafter referred to as "murine SCF protein") and to the purification thereof.

(1. A probe A (SEQ ID NO: 1) and a probe B (SEQ ID NO: 2) were chemically synthesized based on the information on the amino acid and nucleotide sequences (Zsebo et al., *Cell*, vol. 63, p. 213, 1990). The murine SCF protein to be obtained in this Example is the N-terminal side of secretory type SCF protein which has an amino acid sequence shown in SEQ ID NO: 4 and in which the signal peptide and the position-1 Lys has been deleted from the secretory type SCF protein.

Using the above two probes, the SCF gene was isolated from a Balb/c mouse-derived cDNA library by the polymerase chain reaction (PCR) (Mullis et al., *Methods in Enzymol.*, vol. 155, p. 335, 1987). For the expression of the gene fragment of murine SCF protein, a recombinant *E. coli* was prepared in accordance with the procedure disclosed in JP-A-4-502628.

When the nucleotide sequence of the insert was examined for 15 base pairs upstream of its initiation codon (ATG) and 210 base pairs downstream thereof by the dideoxy method (Sanger et al., *Proc. Natl. Acad. Sci. USA*, vol. 74, p. 5463, 1977), it coincided with the sequence shown in SEQ ID NO: 3, revealing that the expected nucleotide sequence has been inserted within the recombinant *E. coli*.

(2) The recombinant organism (55 g by wet weight) after culture was suspended in 500 ml of distilled water and disrupted by homogenizing the suspension 5 times in a laboratory homogenizer (MINI-LAB type 8.30H, manufactured by Rany), with cooling on an ice bath and under a pressure of 8,000 psi. After centrifugation for 10 minutes at 5,000×g and at 4° C., the pellet fraction of the disrupted cells was obtained which was subsequently washed with water twice, resuspended and recentrifuged. The pellet fraction containing the insoluble murine SCF protein was dissolved in 44 ml of 10M urea, 2.75 ml of 1M Tris-HCl (pH 8.5), 8.25 ml of distilled water and 0.84 g of DTT. Insoluble matters were removed by centrifugation for 10 minutes at 10,000×g and at 4° C. The resulting supernatant containing the solubilized murine SCF protein was dialyzed against 50 mM Tris-HCl buffer (pH 8.5) containing 8M urea. After dialysis, insoluble matters were removed by centrifugation for 15 minutes at 16,000×g and at 4° C. To effect the refolding of the solubilized murine SCF protein, the supernatant was added to 5.5 L of a solution A (50 mM Tris-HCl (pH 8.5), 2M urea, 2 mM reduced glutathione, 0.2 mM oxidized glutathione, 1 mM PMSF hydrochloride) and allowed to stand at room temperature for a whole day and night. The obtained solution was concentrated to 1 L using a polysulfone ultrafiltration membrane which has a nominal molecular weight cutoff of 10,000 (manufactured by Millipore) and then adjusted to pH 4 with acetic acid. For the removal of precipitated matters, the centrifugation was then done for 20 minutes at 10,000×g at 4° C. The resulting supernatant was adjusted to pH 8 by addition of Tris powder. The liquid was applied to a column packed with DEAE Serharose FF resin (manufactured by Pharmacia) which has been equilibrated with 20 mM Tris-HCl buffer (pH 8.0), and elution was done by the linear gradient from 0 to 150 mM NaCl in 20 mM Tris-HCl buffer. Ammonium sulfate was added to the thus obtained eluate to a final concentration of 1.2M, and the solution was applied to a column packed with Phenyl Toyopearl resin which has been equilibrated with 20 mM Tris-HCl buffer containing 1.2M ammonium sulfate. The murine SCF protein was eluted by linearly decreasing an ammonium sulfate concentration in the eluate. The eluate obtained was concentrated to 40 ml using an ultrafiltration membrane and subsequently applied to a column packed with Sephacryl S-200 (manufactured by Pharmacia). Dulbecco PBS (manufactured by Nissui Pharmaceutical) was used as the eluting buffer. The murine SCF protein thus obtained was aseptically filtered through a membrane filter having a pore size of 0.22 μm and used as a purified standard in various tests. The yield was approximately 40 mg. When the purified murine SCF protein was examined by SDS-PAGE, a single band was observed on the gel at the position of a molecular weight of approximately 18 kD as expected from the amino acid sequence of the murine SCF protein. In addition, the murine SCF protein retained the activity for stimulating the growth of mast cell (Anderson, M. D. et al., *Cell*, vol. 63, p. 235, 1990).

Example 2

Preparation of murine IL-3 protein

This Example relates to the expression of [Met$^{-1}$] murine IL-3 protein (hereinafter referred to as "murine IL-3 protein") in *E. coli* and to the purification thereof.

(1) A gene coding for the murine IL-3 protein amino acid sequence (Schrader et al., *Ann. Rev. Immunol.*, vol. 4, p. 205, 1986) was chemically synthesized based on the sequence shown in SEQ ID NO: 5.

Using the synthesized DNA, a recombinant *E. coli* strain was prepared in accordance with the procedure disclosed in JP-A-63-269983, and the murine IL-3 protein was expressed.

(2) The recombinant strain (10.5 g by wet weight) after culture was suspended in 20 ml of 20 mM Tris-HCl buffer containing 1 mM DTT and then disrupted in a French press cell-disrupting machine under a pressure of 8,000 psi. After centrifugation for 10 minutes at 5,000×g at 4° C., the precipitate fraction was obtained which was then washed three times with distilled water and subjected to the subsequent operation. The thus obtained precipitate fraction was well suspended in a solution of 1 ml of 1M Tris-HCl buffer (pH 9.2) and 11.5 ml of distilled water. The suspension was mixed with 37.5 ml of 8M guanidine hydrochloride and gently stirred for 1 hour. To the solubilized solution was added 150 ml of 20 mM Tris-HCl buffer (pH 9.2) gradually, followed by addition of 2 mM reduced glutathione and 0.2 mM oxidized glutathione. After 3 days of standing, the solution was fully dialyzed against 20 mM Tris-HCl buffer (pH 7.3), and centrifuged to remove insoluble matters. The supernatant was then applied to a column packed with DEAE Sepharose FF (manufactured by Pharmacia) which has been equilibrated with 20 mM Tris-HCl buffer (pH 7.3) to recover the non-adsorbed fraction. This fraction was dialyzed against 20 mM sodium acetate buffer (pH 5.4) and applied to a column packed with CM Sepharose FF which has been equilibrated with the same dialysis buffer. Thereafter, the elution was done on linear gradient from 100 to 250 mM NaCl in 20 mM sodium acetate buffer (pH 5.4), and the resulting fraction containing the murine IL-3 protein was aseptically filtered in order to be used as a purified standard. The yield was approximately 0.5 mg.

This standard had a specific activity of 4.6×10$^9$ U/mg when measured by a colony assay method using murine bone marrow cells. In addition, when it was examined by SDS-PAGE, a single band was observed on the gel at the position of a molecular weight of approximately 14 kD as expected from the amino acid sequence of the murine IL-3 protein.

Example 3

Preparation of murine GM-CSF protein

This Example relates to the expression of [Met$^{-1}$] murine GM-CSF protein (hereinafter referred to as "murine GM-CSF protein") in *E. coli* and to the purification thereof.

(1) A murine GM-CSF structural gene (SEQ ID NO: 6) was chemically synthesized based on the already published murine GM-CSF amino acid sequence (Miyatake et al., *EMBO J.*, vol. 4, p. 2561, 1985).

The synthesized gene was inserted into the HindIII-BamHI site of a cloning vector pUC18. After confirming its nucleotide sequence, the resulting vector was introduced into *E. coli* in accordance with the procedure disclosed in JP-A-63-269983, and the recombinant murine GM-CSF protein was expressed with the *E. coli*.

(2) 20 g of the cultured recombinant organism was suspended in 45 ml of distilled water and disrupted under a pressure of 8,000 psi. After centrifugation for 10 minutes at 10,000×g at 4° C., the insoluble matters were obtained which were subsequently washed twice with 100 ml of distilled water and then completely dissolved in 20 ml of distilled water, 6.7 ml of 1M Tris-HCl (pH 9.7) and 107 ml of 10M urea. To the solution were added 400 ml of 50 mM Tris-HCl (pH 9.7), 319 mg of reduced glutathione and 97 mg of oxidized glutathione. After standing over a whole day and night at 4° C., the solution was mixed with 26 ml of 1M sodium acetate buffer (pH 5.4) and adjusted to pH 5.4 with 50% acetic acid. To remove insoluble impurities, the centrifugation was done for 10 minutes at 10,000×g at 4° C. The resulting supernatant containing the murine GM-CSF protein was applied to a column packed with CM-Sepharose FF which has been equilibrated with 20 mM sodium acetate buffer, and the elution was done on linear gradient from 0 to 200 mM NaCl in 20 mM sodium acetate buffer (pH 5.4). The eluate containing murine GM-CSF protein was concentrated using an ultrafiltration membrane (manufactured by Amicon) and applied to a column packed with Sephacryl S-200 (manufactured by Pharmacia) which has been equilibrated with Dulbecco PBS pre-adjusted to pH 6 with hydrochloric acid. The equilibrium buffer was used as an eluting buffer. The obtained murine GM-CSF protein was aseptically filtered through a membrane filter having a pore size of 0.22 µm and used as a purified standard in various tests. The final yield was approximately 56 mg.

The activity of the obtained murine GM-CSF protein was confirmed by a colony assay method using murine bone marrow cells. When the murine GM-CSF protein was examined by electrophoresis, a single band was observed on the gel at the position of a molecular weight as expected from the amino acid sequence of the murine GM-CSF protein.

Example 4

Preparation of IL-6 protein

This Example relates to the expression of [Met$^{-1}$ Lys$^{-2}$] human IL-6 protein (hereinafter referred to as "human IL-6 protein") in *E. coli* and to the purification thereof.

(1) A DNA molecule which encodes the human IL-6 amino acid sequence was chemically synthesized in accordance with the procedure of Souza et al. (JP-A-63-500636) with reference to the published amino acid sequence of human IL-6 protein (Haegeman et al., *Eur. J. Biochem.*, vol. 159, p. 625, 1986), and incorporated into *E. coli* to express human IL-6 protein in the same manner as described in JP-A-4-218000. The human IL-6 protein produced by expression in the thus prepared recombinant *E. coli* has a characteristic that a human IL-6 protein starting with Ala at the N-terminus can be produced by cleaving off the N-terminal Met Lys sequence of the IL-6 protein with the protease cathepsin C. Such a treatment, however, was not carried out.

(2) Extraction, solubilization and refolding of human IL-6 protein were carried out in accordance with the procedure of JP-A-63-157996.

The recombinant *E. coli* strain (50 g by wet weight) was suspended in 50 ml of distilled water and disrupted in a French press cell-disrupting machine under a pressure of 8,000 psi. After centrifugation at 5,000×g at 4° C., the precipitate fraction was recovered. The precipitate was suspended in 35 ml of distilled water to which were subsequently added 12 ml of 1M Tris-HCl buffer (pH 8.5) and 180 ml of 8M guanidine hydrochloride solution, followed by gentle stirring. After the precipitate fraction containing human IL-6 protein was completely dissolved, the solution was diluted with 2,500 ml of 20 mM Tris-HCl buffer (pH 8.5). After stirred gently at 4° C. for 18 hours, the solution was concentrated to 400 ml using Pericon Cassette System (manufactured by Millipore) and then dialysed against 20 mM Tris-HCl buffer (pH 9.0). The resulting solution was applied to a Q-Sepharose FF column (10 cm in length and 3 cm in diameter, manufactured by Pharmacia), and elution was effected using 20 mM Tris-HCl buffer containing 300 mM NaCl. Fractions containing human IL-6 protein were collected, dialyzed against 20 mM sodium acetate buffer and then applied to a column (10 cm in height and 3 cm in diameter) packed with CM-Sepharose FF (manufactured by Pharmacia). Elution was done on linear gradient from 0 to 300 mM NaCl in 20 mM sodium acetate buffer. The fractions containing human IL-6 protein were collected and aseptically filtered through a membrane filter having a pore size of 0.22 μm in order to be used in various animal tests. The final yield was approximately 45 mg. When the thus obtained standard was analyzed by SDS-PAGE, a single band was observed on the gel at the position of a molecular weight of around 21 kD as expected from the amino acid sequence of the human IL-6 protein.

The human IL-6 protein standard had a specific activity of $1 \times 10^7$ U/mg when measured based on the IgM-releasing activity from SKW 6.4 cells (Hirano et al., *Proc. Natl. Acad. Sci. USA*, vol. 82, p. 5490, 1985).

Although the murine factors are used in Examples with regard to SCF protein, IL-3 protein and GM-CSF protein, it is of course desirable to use the corresponding human factors when applied to human. We have in fact prepared such human factors. For example, the human SCF protein could be prepared in accordance with the procedure disclosed in JP-A-4-502628, the human GM-CSF protein in accordance with the procedure disclosed in JP-A-63-269983 and the human IL-3 protein in accordance with the procedure disclosed in JP-A-2-482, respectively.

Example of Pharmaceutical Preparations

The recombinant murine SCF protein, murine IL-3 protein, murine GM-CSF protein and human IL-6 protein were mixed and dissolved in 5 ml of PBS, each having a concentration of 6.7 μg/ml, to formulate a pharmaceutical preparation. In a same manner, two types of pharmaceutical preparation for human of the recombinant human SCF protein, human IL-3 protein, human GM-CSF protein, and human IL-6 protein was formulated by mixing and dissolved them in 5 ml of PBS, each having concentration of 6.7 μg/ml (high concentration) and 0.67 μg/ml (low concentration).

Test Examples

1. Male BDF1 mice of 5 to 6-week old (purchased from Charles River Japan) were subjected to whole body irradiation with 8.0 −Gy x-ray (MBR-1520R manufactured by Hitachi Medico: lamp voltage, 150 KV; lamp current, 20 mA; filter, 0.5 mm Al/0.1 mm Cu; focal distance, 35 cm; dosage rate, 3.6 Gy/min). Immediately after the x-ray irradiation, each of the two pharmaceutical compositions formulated in the Example of pharmaceutical preparations was administered into each mouse through its tail vein three times a day (50 μl for each time, 1 μg of each factor/mouse/day) for 6 days. The same amount of PBS was administered to each mouse in the control group. Each of the above three groups was composed of 5 mice. The survival of these mice was observed every day. The mice of the control group started to die after about 2 weeks of the x-ray irradiation and all of them died within 30 days after the irradiation, whereas all animals of the administered groups (this invention) survived even after 30 days of the irradiation (see FIG. 1).

2. A pharmaceutical preparation for human formulated as low concentration in the Example of pharmaceutical preparations is applicable for patients who have hematopoietic disorder caused by having excess dose of radiation. This pharmaceutical preparation as low concentration is administered intravenously three times a day (2 ml for each time, 4 μg of each factor/kg/day) for 14 days.

3. A pharmaceutical preparation for human formulated as high concentration in the Example of pharmaceutical preparations is applicable for malignant patients who have hematopoietic disorder caused by having excess dose of radiation treatment. This pharmaceutical preparation as high concentration is administered subcutaneously (600 μl, 4 μg of each factor/kg/day) for 14 days.

---

What is claimed is:

1. A pharmaceutical composition comprising:
   an effective amount of SCF protein;
   an effective amount of IL-3 protein;
   an effective amount of GM-CSF protein; and
   an effective amount of IL-6 protein,
in combination with a pharmaceutically acceptable carrier.

2. The pharmaceutical composition according to claim 1, wherein the SCF, IL-3, GM-CSF and IL-6 proteins are vertebrate proteins.

3. The pharmaceutical composition according to claim 1, wherein the SCF, IL-3, GM-CSF and IL-6 proteins are mammalian proteins.

4. The pharmaceutical composition according to claim 3, wherein the SCF, IL-3, GM-CSF and IL-6 proteins are human proteins.

5. The pharmaceutical composition according to claim 3, wherein the SCF, IL-3, GM-CSF and IL-6 proteins are murine proteins.

6. The pharmaceutical composition according to claim 3, wherein the SCF, IL-3, proteins are murine proteins and the IL-6 protein is human IL-6 protein.

7. A pharmaceutical composition for treating radiation hazards comprising:
   SCF protein;
   IL-3 protein;
   GM-CSF protein; and
   IL-6 protein
in amounts effective to treat radiation hazards in a patient, in combination with a pharmaceutically acceptable carrier.

8. The pharmaceutical composition according to claim 7, wherein the SCF, IL-3, GM-CSF and IL-6 proteins are human proteins.

9. A method for the treatment of patients with radiation hazards, which comprises administering the pharmaceutical composition according to claim 1 in a therapeutically effective amount to the patients.

10. The method according to claim 9, wherein the SCF, IL-3, GM-CSF and IL-6 proteins are human proteins.

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 56 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

```
AACTCTAGAA    AAAACCAAGG    AGGTAATAAA    TAATGGAGAT    CTGCGGGAAT    CCTGTG                56
```

( 2 ) INFORMATION FOR SEQ ID NO:2:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2:

```
AACCTCGAGC TATTATGCAA CAGGGGGTAA CATAAA                                    36
```

( 2 ) INFORMATION FOR SEQ ID NO:3:

( i ) SEQUENCE CHARACTERISTICS:
       ( A ) LENGTH: 530 base pairs
       ( B ) TYPE: nucleic acid
       ( C ) STRANDEDNESS: double
       ( D ) TOPOLOGY: linear ( i x ) FEATURE:
       ( A ) NAME/KEY: CDS
       ( B ) LOCATION: 28..519

( x i ) SEQUENCE DESCRIPTION: SEQ ID NO:3:

```
CTAGAAAAAC CAAGGAGGTA ATAAATA ATG GAG ATC TGC GGG AAT CCT GTG              51
                                Met Glu Ile Cys Gly Asn Pro Val
                                 1               5

ACT GAT AAT GTA AAA GAC ATT ACA AAA CTG GTG GCA AAT CTT CCA AAT            99
Thr Asp Asn Val Lys Asp Ile Thr Lys Leu Val Ala Asn Leu Pro Asn
     10              15                  20

GAC TAT ATG ATA ACC CTC AAC TAT GTC GCC GGG ATG GAT GTT TTG CCT           147
Asp Tyr Met Ile Thr Leu Asn Tyr Val Ala Gly Met Asp Val Leu Pro
 25              30                  35                      40

AGT CAT TGT TGG CTA CGA GAT ATG GTA ATA CAA TTA TCA CTC AGC TTG           195
Ser His Cys Trp Leu Arg Asp Met Val Ile Gln Leu Ser Leu Ser Leu
             45                  50                  55

ACT ACT CTT CTG GAC AAG TTC TCA AAT ATT TCT GAA GGC TTG AGT AAT           243
Thr Thr Leu Leu Asp Lys Phe Ser Asn Ile Ser Glu Gly Leu Ser Asn
         60                  65                  70

TAC TCC ATC ATA GAC AAA CTT GGG AAA ATA GTG GAT GAC CTC GTG TTA           291
Tyr Ser Ile Ile Asp Lys Leu Gly Lys Ile Val Asp Asp Leu Val Leu
         75                  80                  85

TGC ATG GAA GAA AAC GCA CCG AAG AAT ATA AAA GAA TCT CCG AAG AGG           339
Cys Met Glu Glu Asn Ala Pro Lys Asn Ile Lys Glu Ser Pro Lys Arg
     90                  95                 100

CCA GAA ACT AGA TCC TTT ACT CCT GAA GAA TTC TTT AGT ATT TTC AAT           387
Pro Glu Thr Arg Ser Phe Thr Pro Glu Glu Phe Phe Ser Ile Phe Asn
105                 110                 115                 120

AGA TCC ATT GAT GCC TTT AAG GAC TTT ATG GTG GCA TCT GAC ACT AGT           435
Arg Ser Ile Asp Ala Phe Lys Asp Phe Met Val Ala Ser Asp Thr Ser
                125                 130                 135

GAC TGT GTG CTC TCT TCA ACA TTA GGT CCC GAG AAA GAT TCC AGA GTC           483
Asp Cys Val Leu Ser Ser Thr Leu Gly Pro Glu Lys Asp Ser Arg Val
             140                 145                 150

AGT GTC ACA AAA CCA TTT ATG TTA CCC CCT GTT GCA TAATAGCTCG                529
Ser Val Thr Lys Pro Phe Met Leu Pro Pro Val Ala
         155                 160

A                                                                        530
```

( 2 ) INFORMATION FOR SEQ ID NO:4:

( i ) SEQUENCE CHARACTERISTICS:
       ( A ) LENGTH: 164 amino acids
       ( B ) TYPE: amino acid
       ( D ) TOPOLOGY: linear ( i i ) MOLECULE TYPE: protein ( x i ) SEQUENCE DESCRIPTION: SEQ ID NO:4:

| Met | Glu | Ile | Cys | Gly | Asn | Pro | Val | Thr | Asp | Asn | Val | Lys | Asp | Ile | Thr |
|---|---|---|---|---|---|---|---|---|---|---|---|---|---|---|---|
| 1 | | | | 5 | | | | | 10 | | | | | 15 | |

| Lys | Leu | Val | Ala | Asn | Leu | Pro | Asn | Asp | Tyr | Met | Ile | Thr | Leu | Asn | Tyr |
|---|---|---|---|---|---|---|---|---|---|---|---|---|---|---|---|
| | | | 20 | | | | | 25 | | | | | 30 | | |

| Val | Ala | Gly | Met | Asp | Val | Leu | Pro | Ser | His | Cys | Trp | Leu | Arg | Asp | Met |
|---|---|---|---|---|---|---|---|---|---|---|---|---|---|---|---|
| | | 35 | | | | | 40 | | | | | 45 | | | |

| Val | Ile | Gln | Leu | Ser | Leu | Ser | Leu | Thr | Thr | Leu | Leu | Asp | Lys | Phe | Ser |
|---|---|---|---|---|---|---|---|---|---|---|---|---|---|---|---|
| | 50 | | | | | 55 | | | | | 60 | | | | |

| Asn | Ile | Ser | Glu | Gly | Leu | Ser | Asn | Tyr | Ser | Ile | Ile | Asp | Lys | Leu | Gly |
|---|---|---|---|---|---|---|---|---|---|---|---|---|---|---|---|
| 65 | | | | | 70 | | | | | 75 | | | | | 80 |

| Lys | Ile | Val | Asp | Asp | Leu | Val | Leu | Cys | Met | Glu | Glu | Asn | Ala | Pro | Lys |
|---|---|---|---|---|---|---|---|---|---|---|---|---|---|---|---|
| | | | | 85 | | | | | 90 | | | | | 95 | |

| Asn | Ile | Lys | Glu | Ser | Pro | Lys | Arg | Pro | Glu | Thr | Arg | Ser | Phe | Thr | Pro |
|---|---|---|---|---|---|---|---|---|---|---|---|---|---|---|---|
| | | | 100 | | | | | 105 | | | | | 110 | | |

| Glu | Glu | Phe | Phe | Ser | Ile | Phe | Asn | Arg | Ser | Ile | Asp | Ala | Phe | Lys | Asp |
|---|---|---|---|---|---|---|---|---|---|---|---|---|---|---|---|
| | | 115 | | | | | 120 | | | | | 125 | | | |

| Phe | Met | Val | Ala | Ser | Asp | Thr | Ser | Asp | Cys | Val | Leu | Ser | Ser | Thr | Leu |
|---|---|---|---|---|---|---|---|---|---|---|---|---|---|---|---|
| | 130 | | | | | 135 | | | | | 140 | | | | |

| Gly | Pro | Glu | Lys | Asp | Ser | Arg | Val | Ser | Val | Thr | Lys | Pro | Phe | Met | Leu |
|---|---|---|---|---|---|---|---|---|---|---|---|---|---|---|---|
| 145 | | | | | 150 | | | | | 155 | | | | | 160 |

| Pro | Pro | Val | Ala |
|---|---|---|---|

( 2 ) INFORMATION FOR SEQ ID NO:5:

( i ) SEQUENCE CHARACTERISTICS:
( A ) LENGTH: 453 base pairs
( B ) TYPE: nucleic acid
( C ) STRANDEDNESS: double
( D ) TOPOLOGY: linear ( x i ) SEQUENCE DESCRIPTION: SEQ ID NO:5:

| AAGCTTAAGG | AGGTATATTA | TGGCAAGTAT | TTCAGGACGC | GATACCCATC | GTCTGACCCG | 60 |
|---|---|---|---|---|---|---|
| TACCCTGAAC | TGCAGCAGCA | TCGTTAAAGA | AATTATTGGC | AAGTTGCCGG | AACCTGAACT | 120 |
| GAAAACTGAC | GACGAGGGCC | CTAGCCTGCG | TAACAAATCT | TTTCGTCGTG | TTAACCTGAG | 180 |
| CAAATTCGTT | GAAAGCCAGG | GTGAAGTCGA | CCCTGAAGAT | CGTTACGTAA | TCAAATCTAA | 240 |
| TTACAGAAA | CTGAACTGTT | GTCTGCCGAC | CAGCGCTAAT | GATTCTGCTT | TACCTGGCGT | 300 |
| GTTTATTCGC | GACCTGGATG | ATTTCCGTAA | AAAACTGCGC | TTCTATATGG | TTCACTTAAA | 360 |
| CGATCTTGAA | ACCGTTCTGA | CTTCTAGACC | ACCTCAGCCG | GCTAGCGGTT | CTGTTTCTCC | 420 |
| GAACCGTGGT | ACCGTTGAAT | GCTAATTAGG | ATC | | | 453 |

( 2 ) INFORMATION FOR SEQ ID NO:6:

( i ) SEQUENCE CHARACTERISTICS:
( A ) LENGTH: 406 base pairs
( B ) TYPE: nucleic acid
( C ) STRANDEDNESS: double
( D ) TOPOLOGY: linear ( x i ) SEQUENCE DESCRIPTION: SEQ ID NO:6:

| AAGCTTAAGG | AGGTATATTA | TGGCACCAAC | TCGATCACCC | ATCACTGTCA | CGCGTCCTTG | 60 |
|---|---|---|---|---|---|---|
| GAAGCATGTA | GAGGCCATCA | AGAAGCCCT | GAACCTCCTG | GATGACATGC | CTGTCACGTT | 120 |
| GAATGAAGAG | GTAGAAGTCG | TCTCTAACGA | GTTCTCCTTC | AAGAAGCTAA | CATGTGTGCA | 180 |

| | | | | | |
|---|---|---|---|---|---|
| GACCCGCCTG | AAGATATTCG | AGCAGGGTCT | ACGGGGCAAT | TTCACCAAAC | TCAAGGGCGC | 240
| CTTGAACATG | ACAGCCAGCT | ACTACCAGAC | ATACTGCCCC | CCAACTCCGG | AAACGGACTG | 300
| TGAAACACAA | GTTACCACCT | ATGCGGATTT | CATAGACAGC | CTTAAACCT | TTCTGACTGA | 360
| TATCCCCTTT | GAATGCAAAA | AACCAGGCCA | AAAATGATAA | GGATCC | | 406